(12) United States Patent
Jeffries et al.

(10) Patent No.: US 7,285,403 B2
(45) Date of Patent: Oct. 23, 2007

(54) XYLOSE-FERMENTING RECOMBINANT YEAST STRAINS

(75) Inventors: Thomas W. Jeffries, Madison, WI (US); Haiying Ni, Beijing (CN); Jose Miguel Laplaza, Plymouth, MN (US)

(73) Assignees: Wisconsin Alumni Research Foundation, Madison, WI (US); United States as Represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 11/398,807

(22) Filed: Apr. 6, 2006

(65) Prior Publication Data

US 2006/0228789 A1     Oct. 12, 2006

Related U.S. Application Data

(60) Provisional application No. 60/682,085, filed on May 18, 2005, provisional application No. 60/668,671, filed on Apr. 6, 2005.

(51) Int. Cl.
*C12P 7/06* (2006.01)
*C12Q 1/54* (2006.01)
*C12Q 1/68* (2006.01)
*C12N 1/00* (2006.01)
*C12N 15/63* (2006.01)

(52) U.S. Cl. ............... 435/161; 435/14; 435/41; 435/254.1; 435/255.1; 435/7.31; 435/6; 435/254.21

(58) Field of Classification Search ............ 435/161, 435/14, 471, 254.1, 255.1
See application file for complete search history.

(56) References Cited

U.S. PATENT DOCUMENTS

| | | | |
|---|---|---|---|
| 5,789,210 | A | 8/1998 | Ho et al. |
| 6,071,729 | A | 6/2000 | Jeffries et al. |
| 2003/0157675 | A1 | 8/2003 | Otero |
| 2004/0142456 | A1* | 7/2004 | Jeffries et al. ......... 435/254.21 |

OTHER PUBLICATIONS

Kaneko et al. ( Mol Gen Genet, 1989, 220, 133-139) abstract only.*
Tuleva et al. ( FEMS Microbio. Lett. 1998, 161, 139-144).*
Barua, M. et al., "Partial purification and characterization of a phosphoprotein phosphatase from sperm plasma membrane," Reprod. Fertil. Dev. (1999) 11:379-386.
Bieche, I. et al., "Novel approach to quantitative polymerase chain reaction using real-time detection: application to the detection of gene amplification in breast cancer," Int. J. Cancer (1998) 78:661-666.
Boeke, J.D. et al., "Ty elements transpose through an RNA intermediate," Cell (1985) 40:491-500.
Chang, S.F. and Ho, N.W., "Cloning the yeast xylulokinase gene for the improvement of xylose fermentation," Scientific Note. App. Biochem. Biotechnol. (1988) 17:313-318.
Chiang, L.-C. et al., "D-xylulose fermentation to ethanol by *S. cerevisiae*," Appl. Environ. Microbiol. (1981) 42:284-289.
Cho, J-Y et al., "Pichia stipitis genes for alcohol dehydrogenase with fermentative and respiratory functions," App. Environ. Microbiol. (1998) 64(4):1350-1358.
Cho, K.M. et al., "Delta-integration of endo/exo-glucanase and beta-glucosidase genes into the yeast chromosomes for direct conversion of cellulose to ethanol," Enzyme Microb. Technol. (1999) 25:23-30.
Christianson, T.W. et al., "Multifunctional yeast high-copy-number shuttle vectors," Gene (1992) 110:119-122.
Christova, N. and Galabova, D., "Phosphorylase phosphatase activity in *Saccharomyces cerevisiae*," 257.Z Naturforsch (1998) [C] 53:951-956.
Crabtree, H.G., "Observations of the carbohydrate metabolism in tumors," Biochem. J. (1929) 23:536-545.
De Preter, K. et al., "Quantification of MYCN, DDX1 and NAG gene copy number in neuroblastoma using a real-time quantitative PCR assay," Mod. Pathol. (2002) 15:159-166.
Deng, X.X. and Ho, N.W., "Xylulokinase activity in various yeasts including *Saccharomyces cerevisiae* containing the cloned xylulokinase gene," Scientific Note. Appl. Biochem. Biotechnol. (1990) 24-25:193-199.
Eisen, M.B., et al., "Cluster analysis and display of genome-wide expression patterns," Proc. Natl. Acad. Sci. USA (1998) 94:14863-14868.
Eliasson, A. et al., "Anaerobic xylose fermentation by recombinant *Saccharomyces cerevisiae* carrying XYL1, XYL2, and XKS1 in mineral medium chemostat cultures," App. Environ. Microbiol. (2000) 66:3381-3386.
Epstein, C.B. et al., "Genome-wide responses to mitochondrial dysfunction," Mol. Biol. Cell (2001) 12:297-308.
Forsburg, S.L. and Guarente, L., "Identification and characterization of HAP4: a third component of the CCAAT-bound HAP2/HAP3 heteromer," Genes Dev. (1989) 3:1166-1178.

(Continued)

*Primary Examiner*—Ponnathapu Achutamurthy
*Assistant Examiner*—Younus Meah
(74) *Attorney, Agent, or Firm*—Michael Best & Friedrich LLP

(57) ABSTRACT

Disclosed are xylose-fermenting recombinant yeast strains expressing xylose reductase, xylitol dehydrogenase, and xylulokinase and having reduced expression of PHO13 or a PHO13 ortholog, as well as methods of fermenting xylose to obtain ethanol using the recombinant yeast strains.

9 Claims, 4 Drawing Sheets

OTHER PUBLICATIONS

Hereford, J.B. and Rosbash, M., "Number and distribution of poly-adenylated RNA sequences in yeast," Cell (1977) 10:453-462.

Herrero, P. et al., "Transcriptional regulation of the *Saccharomyces cerevisiae* HXK1, HXK2 and GLK1 genes," Yeast (1995) 11:137-144.

Hinnebusch, A.G., "Translational regulation of yeast GCN4. A window on factors that control initiator-trna binding to the ribosome," J. Biol. Chem. (1997) 272:21661-21664.

Ho, N.W.Y. et al., "Genetically engineered *Saccharomyces* yeast capable of effective cofermentation of glucose and xylose," Appl. Environ. Microbiol. (1998) 64(5):1852-1859.

Hodges, P.E., "The yeast protein database (YPD): a curated proteome database for *Saccharomyces cerevisiae*," Nucleic Acids Res. (1998) 26:68-72.

Hohmann, S. et al., "Evidence for trehalose-6-phosphate-dependent and -independent mechanisms in the control of sugar influx into yeast glycolysis," Mol. Microbiol. (1996) 20:981-991.

Holstege, F.C. et al., "Dissecting the regulatory circuitry of a eukaryotic genome," Cell (1998) 95:717-728.

Horiuchi, H. et al., "High level secretion of a *Rhizopus niveus* aspartic proteinase in *Saccharomyces cerevisiae*," Agric. Biol. Chem. (1990) 54(7):1771-1779.

Huh, W-K et al., "Molecular cloning and functional expression of alternative oxidase from *Candida albicans*," J. Bact. (1999) 181(13):4098-4102.

Ingham, D.J. et al., "Quantitative real-time PCR assay for determining transgene copy number in transformed plants," Biotechniques (2001) 31:132-134, 136-140.

Jin, Y-S. et al., "Genome-wide expression analysis of xylose metabolism in recombinant *Saccharomyces cerevisiae* expressing PsXYL1, PsXYL2, and PsXYL3," (Apr. 28, 2002) XP002376074 [Retrieved from the Internet http://www.ct.ornl.gov/symposium/24th/index_files/O2_04.htm, on Mar. 20, 2006].

Jin, Y.S. and Jeffries, T.W., "Changing flux of xylose metabolites by altering expression of xylose reductase and xylitol dehydrogenase in recombinant *Saccharomyces cerevisiae*," Appl. Biochem. Biotechnol. (2002) 105-108:277-286.

Jin, Y.S. et al., "Molecular cloning of XYL3 (D-xylulokinase) from *Pichia stipitis* and characterization of its physiological function," Appl. Environ. Microbiol (2002) 68:1232-1239.

Jin, Y.S. et al., "Conversion of xylose to ethanol by recombinant *Saccharomyces cerevisiae* containing genes for xylose reductase and xylitol dehydrogenase from *Pichia stipitis*," J. Microbiol. Biotechnol. (2000) 10:564-567.

Jin, Y.S. et al., "Optimal growth and ethanol production from xylose by recombinant *Saccharomyces cerevisiae* require moderate D-xylulokinase activity," Appl. Environ. Microbiol. (2003) 69:495-503.

Johansson, B. et al., "Xylulokinase overexpression in two strains of *Saccharomyces cerevisiae* also expressing xylose reductase and xylitol dehydrogenase and its effect on fermentation of xylose and lignocellulosic hydrolysate," App. Environ. Microbiol. (2001) 67:4249-4255.

Kaneko, Y. et al., "Molecular characterization of a specific p-nitrophenylphosphatase gene, PHO13, and its mapping by chromosome fragmentation in *Saccharomyces cerevisiae*," Mol. Gene. Genet. (1989) 220:133-139.

Kingsman, A.J. and Kingsman, S.M., "Ty: A retroelement moving forward," Cell (1988) 53:333-335.

Kotter, P. and Ciriacy, M., "Xylose fermentation by *Saccharomyces cerevisiae*," Appl. Microbiol. Biotechnol. (1993) 38:776-783.

Kurtzman, C.P., "Molecular taxonomy of the yeasts," Yeast (1994) 10:1727-1740.

Lai, K. and Elsas, L.J., "Overexpression of human UDP-glucose pyrophosphorylase rescues galactose-1-phosphate uridyltransferase-deficient yeast," Biochem. Biophys. Res. Commun. (2000) 271:392-400.

Maleszka, R. and Schneider, H., "Involvement of oxygen and mitochondrial function in the metabolism of D-xylulose by *Saccharomyces cerevisiae*," Arch. Biochem. Biophys. (1984) 228:22-30.

Ndubuisil, M.I. et al., "Characterization of a novel mammalian phosphatase having sequence similarity to *Schizosaccharomyces pombe* PHO2 and *Saccharomyces cerevisiae* PHO13," Biochem. (2002) 41:7841-7848.

Nissen, T.L. et al., "Anaerobic and aerobic batch cultivations of *Saccharomyces cerevisiae* mutants impaired in glycerol synthesis," Yeast (2000) 16:463-474.

Olesen, J. et al., "Yeast HAP2 and HAP3 activators both bind to the CYC1 upstream activation site, UAS2, in an interdependent manner," Cell (1987) 51:953-961.

Parekh, R.N. et al., "An integrating vector for tunable, high copy, stable integration into the dispersed Ty delta sites of *Saccharomyces cerevisiae*," Biotechnol. Prog. (1996) 12:16-21.

Reifenberger, E. et al., "Kinetic characterization of individual hexose transporters of *Saccharomyces cerevisiae* and their relation to the triggering mechanisms of glucose repression," Eur. J. Biochem. (1997) 245:324-333.

Richard, P. et al., "The role of xylulokinase in *Saccharomyces cerevisiae* xylulose catabolism," FEMX Microbiol. Lett. (2000) 190:39-43.

Rizzi, M. et al., "Purification and properties of the NAD+ xylitol dehydrogenase from the yeast *Pichia stipitis* .5," J. Ferment. Bioeng. (1989) 67:20-24.

Rodriguez-Pena, J.M. et al., "The YGR194c (XKS1) gene encodes the xylulokinase from the budding yeast *Saccharomyces cerevisiae*," FEMS Microbiol. Lett. (1998) 162:155-160.

Rose, M.D. et al., "Methods in yeast genetics A Laboratory Course Manual," Cold Spring Harbor, NY: Cold Spring Harbor Laboratory Press (1990).

Senac, T. and Hahn-Hagedahl, B., "Intermediary metabolite concentrations in xylulose- and glucose-fermenting *Saccharomyces cerevisiae* cells," Appl. Environm. Microbiol. (1990) 56:120-126.

Shamanna, D.K. and Sanderson, K.E., "Uptake and catabolism of D-xylose in *Salmonella typhimurium* LT2," J. Bacteriol. (1979) 139:64-70.

Sikorski, R.S. and Hieter, P., "A system of shuttle vectors and yeast host strains designed for efficient manipulation of DNA in *Saccharomyces cerevisiae*," Genetics (1989) 122:19-27.

Tantirungkij, M. et al., "Construction of xylose-assimilating *Saccharomyces cerevisiae*," J. Germent. Bioeng. (1993) 75:83-88.

Tantirungkij, M. et al., "Fed-batch fermentation of xylose by a fast-growing mutant of xylose-assimilating recombinant *Saccharomyces cerevisiae*," Appl. Microbiol. Biotechnol. (1994) 41:8-12.

Taylor, D.R. et al., "Conflicting levels of selection in the accumulation of mitochondrial defects in *Saccharomyces cerevisiae*," PNAS (2002) 99(6):3690-3694.

Teusink, B., "The danger of metabolic pathways with turbo design," Trends Biochem. Sci. (1998) 23:162-169.

Thevelein, J.M. and Hohmann, S., "Trehalose synthase: guard to the gate of glycolysis in yeast?" Trends. Biochem. Sci., (1995) 20:3-10.

Toivari, M.H. et al., "Conversion of xylose to ethanol by recombinant *Saccharomyces cerevisiae*: importance of xylulokinase (XKS1) and oxygen availability," Metab. Eng. (2001) 3:236-249.

Tuleva, B. et al., "A specific alkaline phosphatase from *Saccharomyces cerevisiae* with protein phosphatase activity," FEMS Microbiol. Lett. (1989) 161:139-144.

Walfridsson, M. et al., "Expression of different levels of enzymes from the *Pichia stipitis* XYL1 and XYL2 genes in *Saccharomyces cerevisiae* and its effects on product formation during xylose utilisation," Appl. Microbiol. Biotechnol. (1997) 48:218-224.

Wang, P.P. and Schneider, H., "Growth of yeasts on D-xylulose," Can. J. Microbiol. (1980) 26:1165-1168.

Yang, J. et al., "Characterisation of the specific p-nitrophenylphosphatase gene and protein of *Schizosaccharomyces pombe*," Eur. J. Biochem. (1991) 198:493-497.

\* cited by examiner

XYLOSE-FERMENTING RECOMBINANT YEAST STRAINS

CROSS-REFERENCE TO RELATED APPLICATIONS

This application claims the benefit of U.S. Application Ser. No. 60/668,671, filed Apr. 6, 2005, and U.S. Application Ser. No. 60/682,085, filed May 18, 2005.

STATEMENT REGARDING FEDERALLY SPONSORED RESEARCH OR DEVELOPMENT

This invention was made with United States government support awarded by the following agencies:

The United States Department of Agriculture NRIGCP project number 2001-35504-10695.

The United States has certain rights in this invention.

INTRODUCTION

Within the United States, there is considerable interest in developing alternative energy sources to reduce dependence on foreign oil and nonrenewable energy. The use of ethanol as a fuel has become increasingly prevalent in recent years.

One way to meet the demand for ethanol production is to convert sugars found in biomass (i.e., agricultural wastes, corn hulls, corncobs, and cellulosic materials) to produce ethanol. In biomass conversion, microorganisms are used as biocatalysts to convert cellulosic materials to usable end products, such as ethanol.

Biomass commonly contains xylose at relatively high concentrations. The D-xylose content of hardwood species and herbaceous angiosperms is about 17% and 31% of the total dry weight, respectively. Because agricultural residues, pulping wastes, and fast-growing hardwood species have high xylose contents, the potential economic and ecologic benefits of converting xylose in these renewable materials are significant.

The pentoses D-xylose and L-arabinose are among the most difficult sugars in biomass to metabolize. Bacteria can ferment pentoses to ethanol and other co-products, and bacteria with improved ethanol production from pentose sugars have been genetically engineered. However, these bacteria are sensitive to low pH and high concentrations of ethanol, produce undesired co-products, and produce ethanol at levels too low to make large-scale ethanol production using these bacteria economically feasible.

In general, industrial producers of ethanol strongly favor using yeast as biocatalysts, because yeast fermentations are relatively resistant to contamination, are relatively insensitive to low pH and ethanol, and are easier to handle in large-scale processing. Many different yeast species use xylose respiratively, but only a few species use xylose fermentatively. Fermentation of xylose to ethanol by wild type xylose-fermenting yeast species occurs slowly and results in low yields, relative to fermentation rates and ethanol yields that are obtained with conventional yeasts (e.g., *Saccharomyces cerevisiae*) in glucose fermentations.

The use of *S. cerevisiae* in fermentation affords several advantages over the use of other yeast species. *S. cerevisiae* has been used for centuries in ethanol fermentations, is ethanol tolerant, and is generally regarded as safe. However, native *S. cerevisiae* strains are unable to grow on D-xylose. Attempts to develop a strain of *S. cerevisiae* capable of using xylose have focused on adapting the xylose metabolic pathway from the xylose-utilizing yeasts, such as *Pichia stipitis*.

In *Pichia stipitis*, conversion of xylose to xylulose is catalyzed by two oxidoreductases. Xylose is reduced to xylitol by an $NAD[P]H^+$ linked xylose reductase (XR or PsXYL1), and the xylitol is oxidized to xylulose by an $NAD^+$ linked xylitol dehydrogenase (XD or PsXYL2). Finally, D-xylulokinase (XK or PsXYL3) phosphorylates D-xylulose to form D-xyluose-5-phosphate, which is metabolized further via the pentose phosphate pathway and glycolysis.

Native *S. cerevisiae* strains encode homologs of PsXYL1 and PsXYL2, but they do not express sufficient xylose reductase or xylitol dehydrogenase activity to enable significant growth on xylose. However, *S. cerevisiae* encodes a different xylulokinase (XKS1), which is expressed at a low level, and *S. cerevisiae* is able to grow on and ferment xylulose. Recombinant *S. cerevisiae* expressing PsXYL1 and PsXYL2 was found to grow on xylose (Rodriguez-Pena et al., 1998). However, ethanol production from xylose was not significant because a substantial portion of xylose was converted to xylitol (Jin et al., 2000; Tantirungkij et al., 1994; Kötter and Ciriacy, 1993).

Early reports of xylose fermentation by *S. cerevisiae* indicated that overexpression of xylulokinase (XKS1) is essential to growth on and fermentation of xylose (Chang et al. 1988; Deng et al. 1990). Ho et al. reported that overexpression of the endogenous *S. cerevisiae* xylulose kinase gene (XKS1) along with PsXYL1 and PsXYL2 increased ethanol production and decreased xylitol production from xylose (Ho et al., 1998). Recombinant *S. cerevisiae* transformed with a single copy of PsXYL1 and multiple copies of PsXYL2 accumulate xylulose (Jin and Jeffries, 2002), which suggested that the native level of XK activity in *S. cerevisiae* limits xylose assimilation when PsXYL1 or PsXYL2 is overexpressed.

However, Rodreiguez-Pena et al. showed that overexpression of XKS1 in *S. cerevisiae* inhibits growth on pure D-xylulose (Rodriguez-Pena et al., 1998). Similarly, overexpressing *P. stipitis* XYL3 (PsXYL3) along with high levels of PsXYL1 and PsXYL2 in *S. cerevisiae* was found to completely inhibit cell growth on xylose (Jin et al., 2002), whereas a *S. cerevisiae* transformant expressing PsXYL3 at a moderate level was able to grow on xylose. Johansson et al. found that overexpression of ScXKS1 reduced xylose consumption by 50 to 80% in *S. cerevisiae* transformants, even though it increased the yield of ethanol from xylose, and cautioned against the unmodulated overexpression of ScXKS1 (Johansson et al., 2001). Other studies by Toivari et al. (Toivari et al., 2001) and Richard et al. (Richard et al., 2000) did not show an inhibitory effect from xylulose kinase overexpression.

There remains a need in the art for new yeast strains and methods for fermenting xylose to produce ethanol.

BRIEF SUMMARY OF THE INVENTION

In one aspect, the present invention includes a recombinant xylose-fermenting yeast strain expressing xylose reductase, xylitol dehydrogenase, and xylulokinase and having reduced expression of PHO13 or a PHO13 ortholog, relative to that of its parent strain.

In another aspect, the invention provides a method for producing ethanol by contacting xylose-containing material with a recombinant xylose-fermenting yeast strain expressing xylose reductase, xylitol dehydrogenase, and xyluloki-

DETAILED DESCRIPTION OF THE INVENTION

Figure 1:
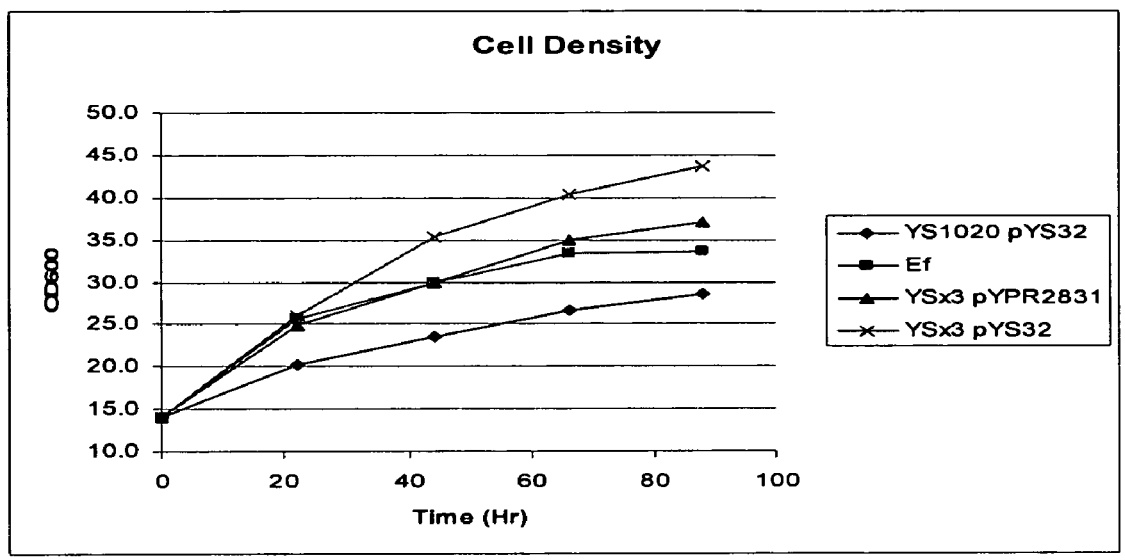
FIG. 1 shows the relative cell density of various yeast strains grown on xylose as a function of time.

Overexpression of PsXYL3 in a *S. cerevisiae* strain expressing PsXYL12 was previously reported to inhibit growth on xylose (Jin et al. 2003). However, spontaneous or chemically induced mutants of a transgenic strain of *S. cerevisiae* engineered to overexpress PsXYL1, PsXYL2, and PsXYL3 were identified that are not susceptible to growth inhibition on xylose. As used herein, *S. cerevisiae* that overexpresses PsXYL1, PsXYL2, or PsXYL3 is one that produces gene or coding sequence transcripts at a level detectably in excess over that of a control cell (e.g., wild type *S. cerevisiae*) grown under the same conditions.

In order to develop and characterize strains of *S. cerevisiae* capable of growth on xylose, transposon mutagenesis was performed on strain *S. cerevisiae* L2612 pYES2-X123, which lacks the ability to grow on xylose and in which *P. stipitis* XYL1, PsXYL2 and PsXYL3 (PsXYL123) are overexpressed, as described below in the Examples. The mutants were screened for the ability to grow on xylose.

Two different types of mutants capable of passing the ability to grow on xylose to their progeny were identified and their respective mutations were further characterized. Two mutants having an mTn insertion at one of two sites in the transaldolase TAL1 promoter were identified. One includes an insertion at −439 and was designated GX312; a second TAL1 promoter mutant includes an insertion at −515 and was designated GX512. Mutant strains GX312 and GX512 were deposited with the Agricultural Research Service Culture Collection in Peoria, Ill. on Sep. 2, 2004 under the Budapest Treaty and assigned accession numbers NRRL Y-30770 and NRRL Y-30769, respectively. We hypothesized that a mutation in the promoter region of TAL1 results in increased expression, which protects against the inhibition of growth on xylose associated with xylulokinase overexpression. Further experiments showed that *S. cerevisiae* L2612 pYES2-X123 transformed with a plasmid overexpressing TAL1 is also capable of growth on xylose.

In addition to insertion mutations at −439 or −515 of the TAL1 promoter region, it is envisioned that other insertion or deletion mutations in the promoter region will result in increased expression of TAL1 and will protect cells overexpressing xylulokinase against growth inhibition on xylose. One wishing to make additional mutants in the TAL1 promoter region could introduce into the promoter by homologous recombination a non-homologous insertion sequence flanked by sequences having homology to portions of the promoter. Because insertion mutations at both −439 and −515 result in increased expression, it is expected that mutants having an insertion sequence between −439 and 515 would overexpress TAL1.

An *S. cerevisiae* strain having the identifying characteristics of NRRL Y-30770 and NRRL Y-30769 is one that overexpresses xylose reductase, xylose dehydrogenase, and xylulokinase, has increased expression of TAL1 relative to wild type expression, and is able to grow better on xylose than a comparable strain overexpressing xylose reductase, xylose dehydrogenase, and xylulokinase and having wild type expression of TAL1. The increased expression of TAL1 may be due to a mutation in the TAL1 promoter or the increased expression may be the result of an increase in TAL1 copy number (e.g., a strain transformed with a sequence encoding TAL1 operably linked to a promoter functional in the yeast strain).

A second type of transposon mutant identified as relieving xylose inhibition of *S. cerevisiae* overexpressing PsXYL123 has an mTn insertion in the PHO13 open reading frame (ORF), which results in reduced expression of full length alkaline phosphatase that has p-nitrophenylphosphatase activity. A mutant constructed with this genotype, designated as DR PHO13, was deposited with the Agricultural Research Service Culture Collection in Peoria, Ill. on Sep. 2, 2004 under the Budapest Treaty and was assigned accession numbers NRRL Y-30771. An *S. cerevisiae* strain having the identifying characteristics of NRRL Y-30771 is one that overexpresses PsXYL123 and has reduced expression of functional PHO13. Such a strain may be developed using transposon mutagenesis or a disruption mutation may be introduced into the PHO13 coding sequence by homologous recombination.

In addition to recombinant *S. cerevisiae*, recombinant strains of economically important, ethanol producing yeast species according to the invention may include, but are not limited to, *Saccharomyces carlsbergensis* (*Saccharomyces pastorianus*), *Saccharomyces uvarum*, *Saccharomyces bayanus* and various hybrids of these and other yeast species used in brewing or winemaking, the thermotolerant yeast, *Kluyveromyces marxianus*, for use in high temperature simultaneous saccharification and fermentation of pretreated lignocellulosic residues, and *Kluyveromyces lactis* for the fermentation of lactose in cheese whey. Strains may be genetically engineered to express increased levels of TAL1 using standard molecular biological techniques to prevent inhibition of growth on xylose associated with XK overexpression.

PHO13 encodes a protein with demonstrated alkaline phosphatase activity (Tuleva et al. 1998). Of approximately 11 substrates tested, PHO13p showed significant hydrolytic activity only against p-nitrophenylphosphate, phosphorylated histone II-A and casein. Tuleva et al. speculated that the physiological role of the PHO13 p-nitrophenylphosphate-specific phosphatase might involve participation in reversible protein phosphorylation. Phosphatases often act on a wide variety of phosphorylated proteins (Barua et al. 1999). The possible role of phosphatases in dephosphorylating histones has been previously noted (Christova et al. 1998). The exact function of Pho13p is unknown, but similar proteins are very widely distributed among yeasts, fungi and other organisms. A BLAST analysis of Pho13p identified 13 closely related proteins produced by *Debaryomyces hansenii, Gibberella zeae, Ustilago maydis, Schizosaccharomyces pombe, Neurospora crassa, Candida albicans, Yarrowia lipolytica, Ashbya gossypii, Kluyveromyces lactis, Candida glabrata,* and *Saccharomyces cerevisiae*. More than 100 similar proteins are known from many other organisms. These proteins have not yet been fully characterized with respect to their activities. However, it is reasonably expected these proteins will be identified as orthologs having a similar structure and function to Pho13p, and that isolates overexpressing enzymes associated with xylose fermentation and having disrupted Pho13 will exhibit improved xylose fermentation.

A yeast sequence encoding PHO13 ortholog may be disrupted using homologous recombination for those species for which a homologous putative translation product has been published. Alternatively, the PHO13 ortholog p-nitrophenylphosphatase may be identified from a genomic library using degenerative oligonucleotide probes and sequenced or partially sequence to permit design of a disruption cassette to disrupt the in vivo coding sequence.

It is expected that recombinant yeast strains of the present invention may be further manipulated to achieve other desirable characteristics, or even higher specific ethanol yields. For example, selection of recombinant yeast strains by sequentially transferring the mutant yeast strains of the present invention on medium containing hydrolysate or by growing them in continuous culture under selective conditions may result in improved yeast with enhanced fermentation rates. Suitably, the recombinant yeast strain is able to grow under conditions similar to those found in industrial sources of xylose. In the practice of the method of the present invention, the xylose-containing material can be inoculated with a suitable recombinant *Saccharomyces cerevisiae* without excessive manipulation. By way of example, the pulping industry generates large amounts of cellulosic waste. Saccharification of the cellulose by acid hydrolysis yields hexoses and pentoses that can be used in fermentation reactions. However, the hydrolysate or sulfite liquor contains high concentrations of sulfite and phenolic inhibitors, which inhibit or prevent the growth of most organisms. Sequential transfers or continuous culture of the yeast selects for strains that are better able to grow in the presence of sulfite or phenolic inhibitors. Likewise, sequentially transferring or continuously cultivating the recombinant yeast under conditions that would select for faster fermentation could reasonably be expected to obtain further improvements. Such conditions would include cultivation on xylose under oxygen limitation or anaerobiosis in the presence or absence of glucose.

By "xylose-containing material," it is meant any medium comprising xylose, whether liquid or solid. Suitable xylose-containing materials include, but are not limited to, hydrolysates of polysaccharide or lignocellulosic biomass such as corn hulls, wood, paper, agricultural by-products, and the like.

The following non-limiting Examples are intended to be purely illustrative.

EXAMPLES

Microbial strains, primers and plasmids. *Saccharomyces cerevisiae* L2612 (MATα leu2-3 leu2-112 ura3-52 trp1-298 can1cyn1 gal$^+$) was the parental strain. *Saccharomyces cerevisiae* YS1020 (MATα leu2-3 leu2::LEU2-TDH3 - PsXYL1-TDH3$_T$ ura3:: URA3-TDH3$_T$-PsXYL2-TDH3$_T^p$ trp1-298 can1 cyn1 gal$^+$) was used as the recipient host for control experiments and as the parental strain for making. *S. cerevisiae* YSX3 (MATα leu2-3 leu2::LEU2 TDH3 - PsXYL1-TDH3$_T$ ura3::TDH3$_p$-PsXYL2-TDH3$_T$ Ty3$^p$:: G418$^R$-PsXYL3 trp1-298 can1 cyn1 gal$^+$) was developed in a previous study (Jin et al. 2003). *Escherichia coli* DH5α was used for plasmid preparation. The primers and plasmids used in this study are listed in Tables 1 and 2.

Media. Yeast strains without plasmids were grown on YPD (yeast extract 20 g/L, peptone 10 g/L and glucose 20 g/L). Strains with plasmids carrying TRP1 and/or URA3 markers were grown on yeast selection medium (YS), which was made of yeast nitrogen base (YNB) and casamino acids (10 g/L), supplemented with glucose (20 g/L) or xylose (20 g/L for growth test, 40 g/L for fermentation). Complete synthetic mix (CSM) without certain amino acids and nucleotides was used to select other auxotrophic markers.

Enzymes, primers and chemicals. Restriction enzymes, DNA modifying enzymes and other molecular reagents were obtained from New England Biolabs (Beverly, Mass.), Promega (Madison, Wis.), Stratagene (La Jolla, Calif.) or Roche Biochemical (Indianapolis, Ind.). Reaction conditions employed were as recommended by the suppliers. All general chemicals were purchased from Sigma (St. Louis, Mo.). Sigma-Genosys (The Woodlands, Tex.) and Invitrogen (Carlsbad, Calif.) synthesized the primers for PCR and sequencing.

Overexpression of PsXYL3 in *S. cerevisiae* YSX3. pYS32 was transformed into YSX3 using the lithium acetate-heat shock method. The transformants were selected on YS dextrose (YSD).

Insertional mutagenesis. The mTn-IacZ/LEU2-mutagenized library was obtained from Yale Genome Analysis Center (New Haven, Conn. 06520). Plasmid DNA from the pools of the mTn inserted genomic library was digested with NotI to release the mutated insertional library of *S. cerevisiae* genes from the bacterial vector. The digested DNA was purified with a GENECLEAN® Kit from Qbiogene (Carlsbad, Calif. 92008). The strain for mutagenesis, *S. cerevisiae* L2612 pYES2-X123, was grown on YSD+Trp to an optical density (OD) 600 nm of between 1 and 2. Cells grew faster in this medium than in YNBG+CSM-Ura (without uracil). However, either medium could prevent the plasmid with URA3 from being lost. Digested library DNA was transformed following the lithium acetate-heat shock protocol described by Agatep et al. (1998) After transformation, cells were incubated in YSD+Trp for one doubling (≈4 hrs). Then cells were harvested, washed and re-suspended in water. A portion (1%) of the cell suspension was plated onto YNBG+CSM-Leu-Trp to count the number of total transformants. The remainder of the cell suspension was plated onto YNBX+CSM-Leu-Trp to screen for mutants that would grow on the xylose plates.

Identification of the insertion site. The mutants were plated on YPD+5' fluoroorotic acid (FOA) to cure pYES2-X123. The resulting colonies were plated on YSD+Trp to make sure that they were ura-. The vector pRSQ2-URA3 was linearized with BamHI, which leaves a portion of lacZ at either end. Linearized pRSQ2-URA3 was purified using the GENECLEAN Kit and transformed into the URA3 cured mutants by lithium acetate-heat shock, whereupon it integrated into the transposon-borne lacZ sequence. Total DNA was recovered from the transformants following incubation with proteinase K, SDS, and RNase A, followed by adjusting the NaCl concentration to 0.2 mol/L and precipitation with 2 volume of cold absolute ethanol.

For plasmid rescue, 5 μg DNA was digested with a restriction enzyme having a recognition sequence in the polylinker of pRSQ2-URA3 (i.e., ClaI, EcoR1, EcoRV, HindIII, KpnI, PstI, SalI or XhoI), resulting in the release of a linear fragment containing the bacterial replication origin, β-lactamase gene, a portion of lacZ and adjacent yeast DNA. The digestion mixture was heated to inactivate the restriction enzyme using the conditions recommended in the NEB Catalog, cooled on ice, and purified by ethanol precipitation. The DNA pellet was dissolved in water. Ligation was conducted by incubating DNA (2 to 10 µg/ml) with T4 DNA ligase buffer and T4 DNA ligase (2 units/µl) at 16° C. overnight. A low DNA concentration was selected to promote intramolecular ligation. Following ligation, DNA was purified by ethanol precipitation and the DNA pellet resuspended in 10 µl water. One-half (5 µl) was used to transform E. coli DH5α by electroporation. The transformants were selected for ampicillin resistance. DNA from plasmid minipreps was analyzed by double digestion with BamHI and the rescue enzyme, which could release a piece of pRSQ2-URA3. The plasmids that appeared to have the correct restriction pattern were sequenced using a primer from the lacZ sequence in pRSQ2-URA3. If plasmids could not be properly rescued, another rescue enzyme was tried. Sequences were identified using the BLAST algorithm on the NCBI web site (http://www.ncbi.nlm.nih.gov/BLAST/).

Confirmation of transposition event. To confirm that the insertion rather than a spontaneous mutation enabled growth on xylose, we transferred the transposon insertion along with the genomic flanking regions back to the parental strain to see if it resulted in the same phenotype.

To rescue the whole insertion site from the genomic DNA preparation, a restriction enzyme was selected that would not cut neither mTn-lacZ/LEU2 nor pRSQ2-URA3, but which would cut at sites flanking each side of the insertion site in yeast DNA. The resulting large plasmid was recovered by transformation into E. coli and then digested with the rescue enzyme and transformed into L2612. The transformants were selected on YNBG+CSM-Leu-Ura plates. Four transformants were selected to confirm each mutation. pRS424-X123 was transformed into each transformant and the transformants receiving pRS424-X123 were selected on YSD plates, and their growth on YSX plates was evaluated.

Subcloning the mutant TAL1 into a plasmid. For mutants designated Mut312 and Mut512, which contain mTn insertion upstream of TAL1, PstI was used to rescue the insertion sites. The resulting plasmids were named pRSQ312 and pRSQ512, respectively. Each was digested with DraI, which cuts in the Amp ORF, and EcoRV, which cuts in the pRSQ2-URA3 polylinker, to release a fragment containing the N-terminal region of Amp, the full LacZ ORF from pRSQ2-URA3, the TAL1 promoter containing the mTn insertion, and the TAL1 ORF and terminator (400 bp to Pst1 site). The fragment was subcloned into the SmaI site of pRS314 and the resulting plasmids were named pRS314-312tal and pRS314-512tal.

PHO13 Knockout. The plasmid used for the PHO13 knockout was subcloned in three steps. First, LEU2 was excised from pRS315 with AccI and DraIII, and inserted into the SmaI site of pBluescript (pBlue-LEU2). Second, a fragment containing the PHO13 ORF C-terminal 180 bp and the 250 bp terminator was inserted between the PstI and XhoI sites of pBlue-LEU2 by blunt end ligation (pBlue-LEU2-PHO13 C). Finally, a XhoI fragment, which was from −60 to −1680 upstream of PHO13, was inserted between SacI and SpeI sites of pBlue-LEU2-PHO13 C by blunt end ligation (pBlue-DR PHO13). In each step, the orientation of the insert was determined by restriction analysis and the correct orientation was selected. In pBlue-DR PHO13, PHO13 upstream, LEU2 and PHO13 C-terminal and terminator all were oriented in the same direction. pBlue-DR PHO13 was digested with HindIII and ScaI to release a fragment containing PHO13 upstream −1220 to −60 bp, LEU2 and PHO13 ORF and terminator 250 bp. The digested DNA was transformed into L2612. The transformants were selected on YNBG+CSM-Leu plates.

Genomic DNA was prepared from several transformants. PHO13 knockout mutants were confirmed by PCR using primers between the PHO13 promoter and the LEU2 promoter, which gave a PCR product of the expected size. In contrast, when primers between the PHO13 promoter and the PHO13 ORF were used, no PCR product was obtained. The correct strain was named DR PHO13.

Xylose fermentation. Yeast strains were grown on YSD+Ura medium. Cells were harvested, washed with and inoculated into YSX+Ura (40 g/L xylose). The culture was 50 ml in 125 ml flask in triplicate. Shaking speed was 200 rpm. The xylose and xylitol concentrations in fermentation samples were determined by high-performance liquid chromatography (HPLC) while the ethanol concentrations were determined by gas chromatography (GC).

Overexpression of PsXYL3 in Saccharomyces cerevisiae YSX3. S. cerevisiae YS1020 was constructed by integrating PsXYL12 under the strong ScGAPDH promoter, $TDH3_p$. PsXYL3 with its native promoter was randomly integrated into YS1020 chromosome. S. cerevisiae YSX3 was selected from the resulting strains for its fast growth on and ethanol production from xylose. Our previous study showed that overexpression of PsXYL3 in YS1020 inhibited growth on and ethanol production from xylose (Jin et al. 2003), a finding confirmed in subsequent trials. Because xylulokinase is an essential enzyme in xylose metabolism, we concluded that moderate xylulokinase level made YSX3 a good xylose-fermenting strain. To test this conclusion, we overexpressed PsXYL3 by plasmid transformation in the YSX3 background. Surprisingly, the transformant, YSX3(pYS32), could also grow on xylose (FIG. 1). YS1020(pYS32), which expresses xylulokinase at a high level and barely grows on xylose, was plated on xylose and a few colonies ($\approx$1 in $10^6$ colony forming units) capable of growth on xylose were obtained. One of these colonies, which we assumed to be spontaneous mutants, was designated "Ef".

Figure 2:
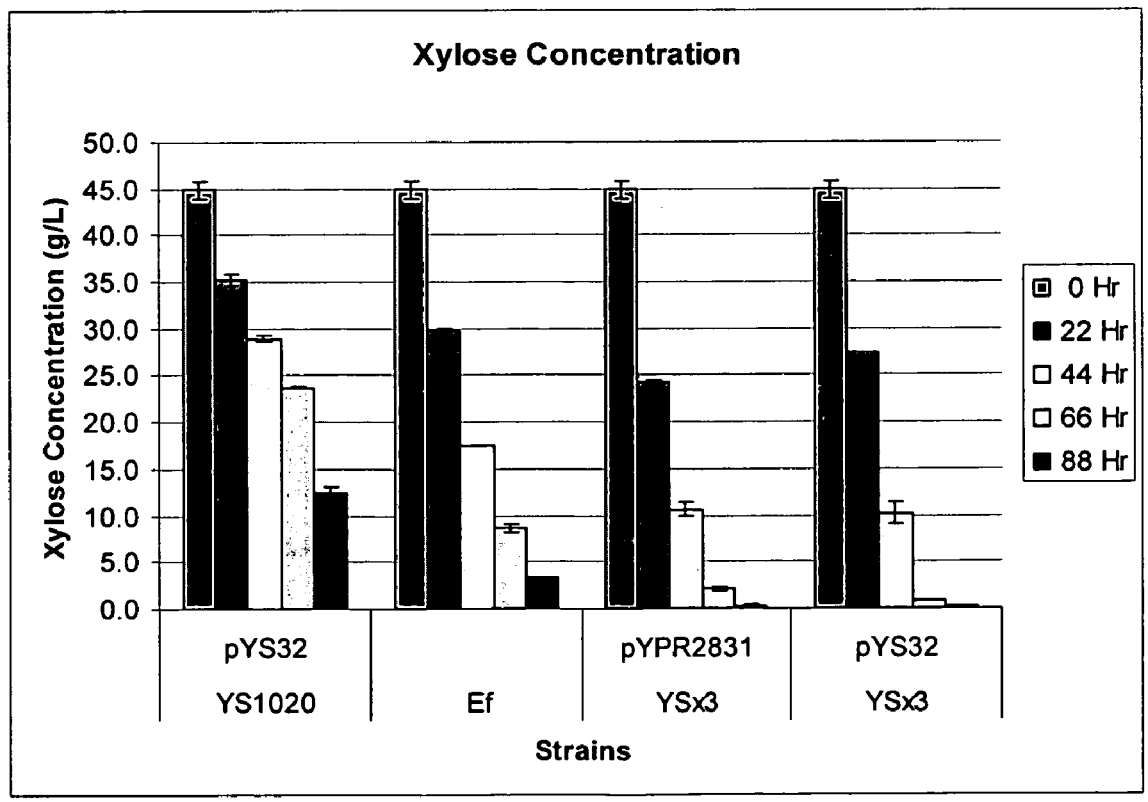
FIG. 2 shows xylose consumption by various yeast strains as a function of time.
Figure 3:
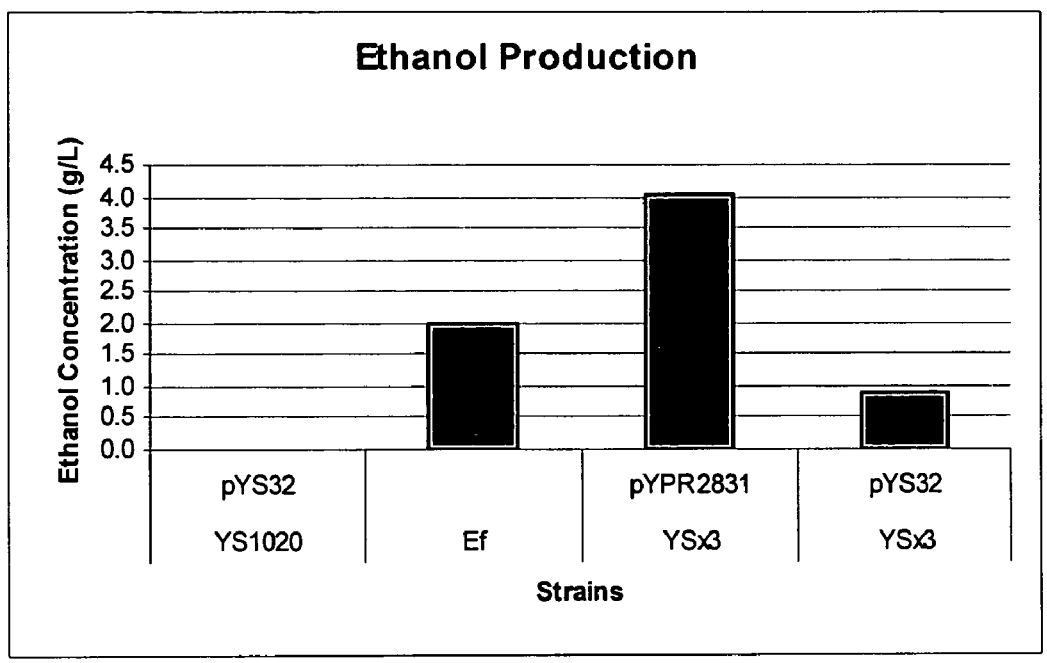
FIG. 3 shows ethanol concentration (g/l) in fermentation reactions using various yeast strains.

Fermentation data showed that YSX3 transformants consumed xylose quickly, no matter how much xylulokinase was expressed (FIG. 2). However, YSX3(pYS32) produced little ethanol from xylose relative to YSX3(YPR2831) (FIG. 3). Because YSX3(pYS32) grew faster, more xylose was converted into cell mass. This suggested that the growth advantage of YSX3 on xylose was not due to its moderate xylulokinase level but that this might result from a mutation that conferred resistance to xylulokinase overexpression. However, moderate xylulokinase level might be necessary for high ethanol production.

Insertional mutagenesis. S. cerevisiae L2612 pYES2-X123, which barely grows on xylose, was used as the parental strain for mutagenesis. After transforming the mTn inserted genomic library, we selected mutants that grew on xylose. The insertion sites in these mutants were identified by plasmid rescue and sequencing. To confirm that it was the insertion rather than spontaneous mutations that caused the phenotype, we transferred the insertion back to the parental strain. If overexpression of PsXYL123 still caused growth inhibition on xylose, the insertion site was eliminated. The confirmed mutants had mTn insertions upstream of the TAL1 ORF or in the PHO13 ORF (Table 3).

TAL1 overexpression. To evaluate whether the mTn insertion upstream of TAL1 affected TAL1 expression, transformants containing two copies of TAL1 were constructed. Plasmids carrying a mutant TAL1, pRS314-312tal and pRS314-512tal, were made from Mut312 and Mut512, respectively, and transformed into L2612 pYES2-X123. The transformants contained heterodiploid TAL1, with a mutant copy on the plasmid and a wild-type copy on the chromosome. The transformants could grow on xylose, suggesting that the mutant copy of TAL1 was dominant with respect to growth on xylose. mTn insertion at TAL1 upstream might enhance TAL1 expression in the strain overexpressing PsXYL123 when grown on xylose. To test this possibility, pRS314-ADHtal, which carries TAL1 under constitutive strong ADH1 promoter, was transformed into L2612 pYES2-X123. As expected, the transformant could grow on xylose. Therefore, increasing TAL1 expression may relieve the growth inhibition on xylose.

Figure 4:
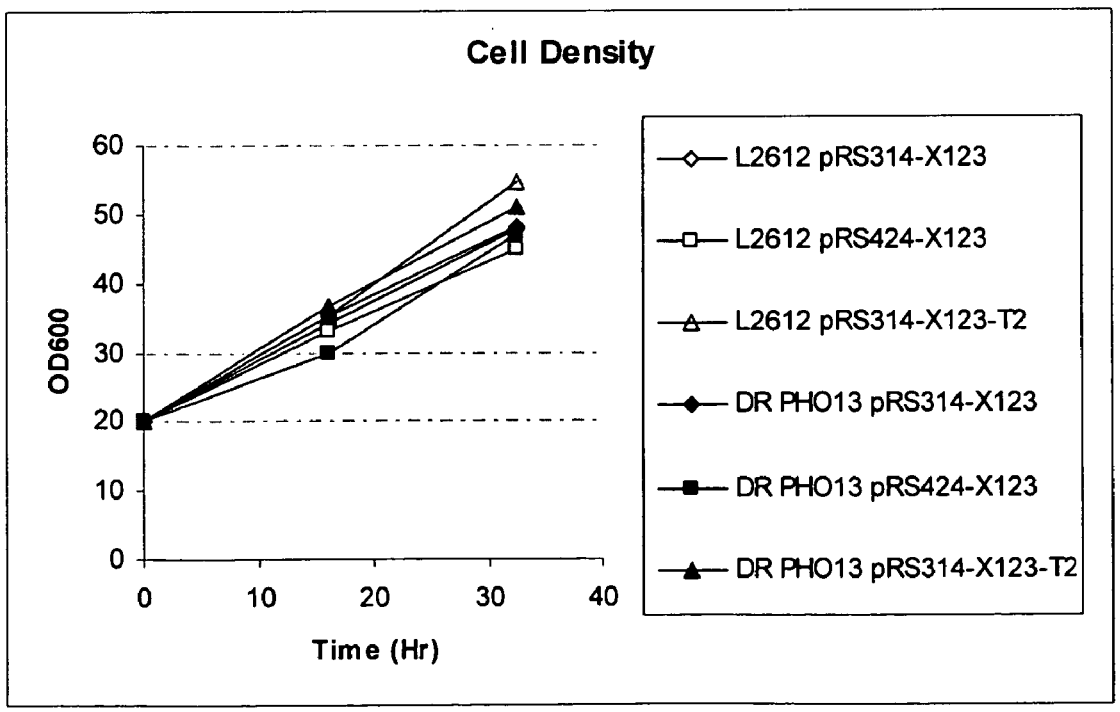
FIG. 4 shows cell growth of various yeast strains as a function of time.

Complete knockout of PHO13. Mut1101 and Mut1201 contain mTn inserted into the PHO13 ORF. However, a large part of the PHO13 gene product could still be synthesized. To determine whether deleting the complete gene would have the same effect, we made a pho13 knockout mutation in L2612, and transformed it with pYES2-X123. This transformant grew well on xylose, like the mutants with mTn insertion (FIG. 4). Therefore, reduced PHO13 expression appears to relieve growth inhibition on xylose.

Figure 5:
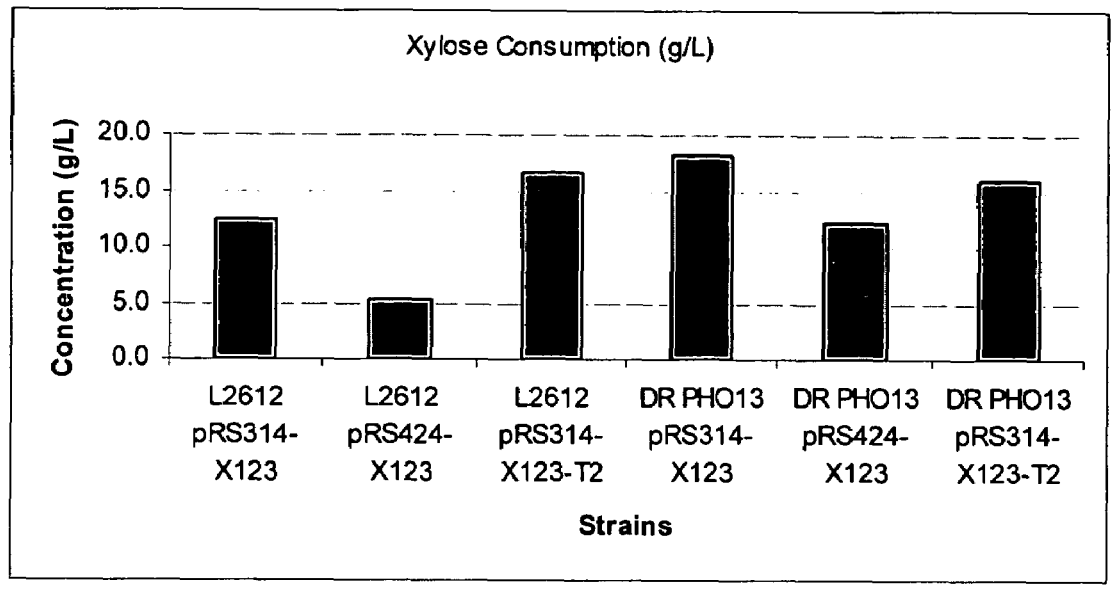
FIG. 5 shows xylose consumption by various yeast strains.
Figure 6:
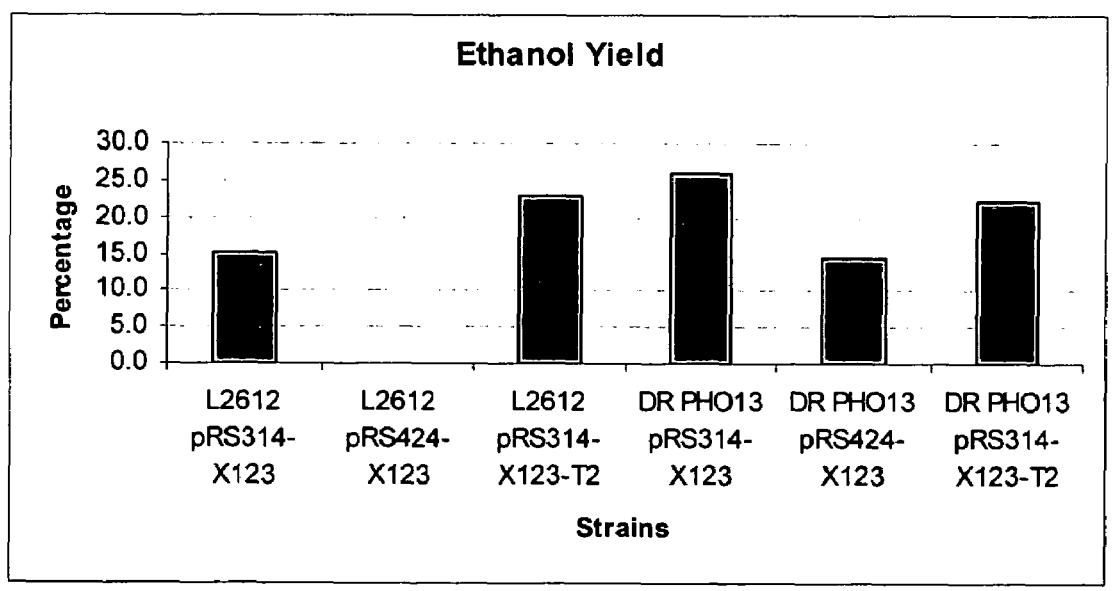
FIG. 6 shows ethanol yield (grams ethanol produced/gram xylose consumed) from fermentations by various yeast strains.
Figure 7:
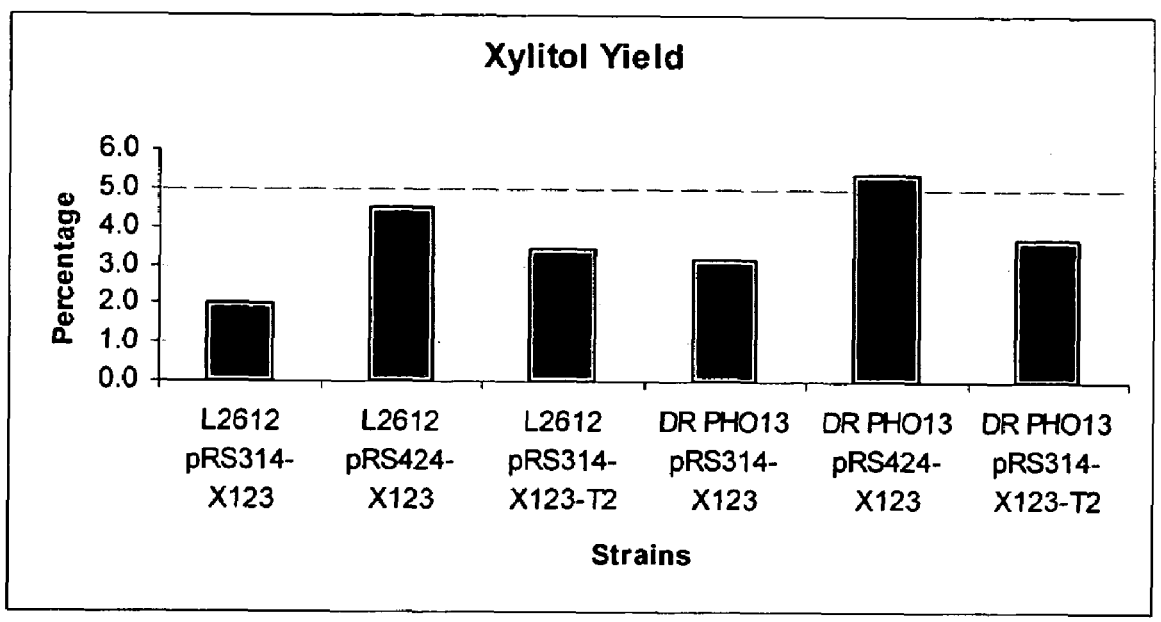
FIG. 7 shows xylitol yield (grams xylitol produced/gram xylose consumed) from fermentations by various yeast strains.

Xylose fermentation of the transformants with pho13 knockout mutation. Fermentation was conducted using six transformants made from 2 strains (L2612 and DR PHO13) and 3 plasmids (pRS314-X123, pRS424-X123 and pRS314-X123-T2 (T2: TAL1 and TKL1)). There was little difference in cell growth among the six strains. Regardless of PHO13 status, pRS424-X123 transformants showed reduced xylose consumption (FIG. 5), lower ethanol yield (FIG. 6), and higher xylitol yield (FIG. 7) than transformants with other plasmids. However, of these two strains, the DR PHO13 (pRS424-X123) transformant consumed more xylose, and produced more ethanol and xylitol than the L2612(pRS424-X123) transformant, which produced no ethanol. Xylose consumption as well as ethanol and xylitol yields were comparable for the two pRS314-X123-T2 transformants. Xylose consumption and ethanol yield of L2612(pRS314-X123) was greater than that of DR PHO13(pRS314-X123), whereas xylitol yields for the two recombinant strains were similar.

Overexpression of PsXYL123 (e.g., in a multiple-copy plasmid) inhibits xylose fermentation in L2612, whereas xylose fermentation is greater in the PHO13 knockout strain, DR PHO13. The PHO13 knockout also improved xylose fermentation when PsXYL123 was expressed at a moderate level (in single-copy plasmid). However, increased expression of TAL1 and TKL1 (transketolase) in a PHO13 knockout did not exhibit an additive or synergistic effect.

TABLE 1

Oligonucleotides used in this study

| Name | Sequence | Utility |
| --- | --- | --- |
| LacZ | tgtgctgcaaggcgattaag (SEQ ID NO:1) | Sequence insertion site from mTn |
| LEU2-S20C | gaacacatgaacaaggaag (SEQ ID NO:2) | PCR from LEU2 promoter to upstream |
| PHO13 | ggatcctggtggaaactattt | PCR from PHO13 pro- |

TABLE 1-continued

Oligonucleotides used in this study

| Name | Sequence | Utility |
| --- | --- | --- |
| N1 | ctc g (SEQ ID NO:3) | moter to downstream |
| PHO13 C2 | ccaacaaagtgaacagaatcc (SEQ ID NO:4) | PCR from middle of PHO 13 ORF to upstream |

TABLE 2

Plasmids used in this study

| Name | Function | Structural elements |
| --- | --- | --- |
| pRS314 TRPI | Centromere | |
| pRS424 TRPI | 2μ origin | |
| pYPR2831 TRPI | 2μ origin | TDH3$_P$-TDH3$_T$ |
| pYS32 TRPI | 2μ origin, | TDH3$_P$-PsXYL3-TDH3$_T$ |
| pRS314-X123 | TRPI, Centromere | TDH3$_P$-PsXYL1-TDH3$_T$, TDH3$_P$-PsXYL2-TDH3$_T$, TDH3$_P$-PsXYL3-TDH3$_T$ |
| pRS314-X123-T2 | TRP1, Centromere | TDH3$_P$-PsXYL1-TDH3$_T$, TDH3$_P$-PsXYL2-TDH3$_T$, TDH3$_P$-PsXYL3-TDH3$_T$, TDH3$_P$-ScTAL1-CYC1$_T$, TDH3$_P$-ScTKL1-CYC1$_T$ |
| pRS424-X123 | TRP1 2μ origin | TDH3p-PsXYL1-TDH3T, TDH3p-PsXYL2-TDH3T, TDH3p-PsXYL3-TDH3T |
| pYES2 | URA3 2μ origin | |
| pYES2-X123 | URA3 2μ origin | TDH3$_P$-PsXYL1-TDH3$_T$, TDH3$_P$-PsXYL2-TDH3$_T$, TDH3$_P$-PsXYL3-TDH3$_T$ |
| pRSQ2-URA3 | Integration vector | |
| pRS314-312tal | TRP1, Centromere | ScTAL1 with upstream insertion from Mut312 |
| pRS314-512tal | Trp1, Centromere | ScTAL1 with upstream insertion from Mut512 |
| pRS314-ADHtal | TRP1, Centromere | ADH1$_P$-SCTAL1-CYC1$_T$ |
| pBlue-DR PHO13 | pBluescript | PHO13$_P$-LEU2-PHO13$_T$ |

TABLE 3 mTn Insertional Mutants

| Mutant | Growth on Xylose | Insertion Site | Other Experiments |
| --- | --- | --- | --- |
| 312 | Medium | TAL1 Promoter −439 | Dominant |
| 512 | Medium | TAL1 Promoter −515 | Dominant |
| 1101 | Very Fast | PHO13 ORF 252/312 aa | pho13 knockout |
| 1201 | Very Fast | PHO13 ORF 229/312 aa | also grows on xylose |

PUBLICATIONS CITED

Agatep, R., Kirkpatrick, R. D., Parchaliuk, D. L., Woods, R. A. and Gietz, R. D. (1998) Transformation of *Saccharomyces cerevisiae* by the lithium acetate/single-stranded carrier DNA/polyethylene glycol (LiAc/ss-DNA/PEG) protocol. Technical Tips Online (http://tto.trends.com) for this method.

Barua, M., A. K. Ghosh, and G. C. Majumder. 1999. Partial purification and characterization of a phosphoprotein phosphatase from sperm plasma membrane. Reprod Fertil Dev 11:379-86.

Chang, S. F., and Ho, N. W. (1988) Cloning the yeast xylulokinase gene for the improvement of xylose fermentation. Scientific Note. *Appl. Biochem Biotechnol* 17: 313-318.

Christova, N., and D. Galabova. 1998. Phosphorylase phosphatase activity in *Saccharomyces cerevisiae* 257. Z Naturforsch [C] 53:951-6.

Deng, X. X., Ho, N. W. (1990) Xylulokinase activity in various yeasts including *Saccharomyces cerevisiae* containing the cloned xylulokinase gene. Scientific Note. *Appl. Biochem Biotechnol.* 24-25: 193-199.

Jin, Y. S. and Jeffries, T. W. (2002) Changing flux of xylose metabolites by altering expression of xylose reductase and xylitol dehydrogenase in recombinant *Saccharomyces cerevisiae; Appl. Biochem. Biotechnol.* 105-108:277-286.

Jin, Y. S., Jones, S. Shi, N. Q. and Jeffries, T. W. (2002) Molecular cloning of XYL3 (D-xylulokinase) from *Pichia stipitis* and characterization of its physiological function. *Appl. Environ. Microbiol.* 68.

Jin, Y. S., Lee, T. H., Choi, Y. D., Ryu, Y. W. and Seo, J. H. (2000) Conversion of xylose to ethanol by recombinant *Saccharomyces cerevisiae* containing genes for xylose reductase and xylitol dehydrogenase from *Pichia stipitis. J. Microbiol. Biotechnol.* 10:564-567.

Jin, Y. S., Ni, H., Laplaza, J. M., and Jeffries, T. W. (2003) Optimal growth and ethanol production from xylose by recombinant *Saccharomyces cerevisiae* require moderate D-xylulokinase activity. *Appl. Environ. Microbiol.* 69:495-503.

Johansson, B., Christensson, C., Hobley, T. and Hahn-Hägerdal, B. (2001) Xylulokinase overexpression in two strains of *Saccharomyces cerevisiae* also expressing xylose reductase and xylitol dehydrogenase and its effect on fermentation of xylose and lignocellulosic hydrolysate. *Appl. Environ. Microbiol.* 67: 4249-4255.

Kötter, P. and Ciriacy, M. (1993) Xylose fermentation by *Saccharomyces cerevisiae. Appl. Microbiol. Biotechnol.* 38: 776-783.

Richard, P., Toivari, M. H. and Penttila, M. (2000) The role of xylulokinase in *Saccharomyces cerevisiae* xylulose catabolism. *FEMS Microbiol. Lett.* 190: 39-43.

Rodriguez-Pena, J. M., Cid, V. J., Arroyo, J. and Nombela, C. (1998) The YGR194c (XKS1) gene encodes the xylulokinase from the budding yeast *Saccharomyces cerevisiae. FEMS Microbiol. Lett.* 162: 155-160.

Tantirungkij, M., Izuishi, T., Seki, T. and Yoshida, T. (1994) Fed-batch fermentation of xylose by a fast-growing mutant of xylose-assimilating recombinant *Saccharomyces cerevisiae. Appl. Microbiol. Biotechnol.* 41: 8-12.

Toivari, M. H., Aristidou, A., Ruohonen, L. and Penttila, M. (2001) Conversion of xylose to ethanol by recombinant *Saccharomyces cerevisiae:* importance of xylulokinase (XKS1) and oxygen availability. *Metab. Eng.* 3: 236-249.

Tuleva, B., E. Vasileva-Tonkova, and D. Galabova. 1998. A specific alkaline phosphatase from *Saccharomyces cerevisiae* with protein phosphatase activity. FEMS Microbiol Lett 161:139-44.

We claim:

1. A recombinant xylose-fermenting strain of *Saccharomyces cerevisiae* expressing Pichiastipis XYL123 and having a transposon or disruption mutation in PHO13.

2. The strain of claim 1, wherein the strain is deposited as NRRL Y-30771.

3. The strain of claim 1, wherein the strain ferments xylose to ethanol at a higher rate than the rate of its parent strain.

4. A yeast strain deposited as NRRL Y-30769 or NRRL Y-30770.

5. A method for producing ethanol comprising:
  contacting xylose-containing material with a yeast strain deposited as NRRL Y-30769, a yeast strain deposited as NRRL Y-30770, or a strain of claim 1 under suitable conditions for a period of time sufficient to allow fermentation of at least a portion of the xylose to ethanol.

6. The method of claim 5, wherein the yeast strain comprises the strain of claim 1.

7. The method of claim 5, wherein the recombinant strain comprises the strain deposited as NRRL Y-30769.

8. The method of claim 5, wherein the recombinant strain comprises the strain deposited as NRRL Y-30770.

9. The method of claim 5, wherein the recombinant strain comprises the strain deposited as NRRL Y-30771.

* * * * *

UNITED STATES PATENT AND TRADEMARK OFFICE
CERTIFICATE OF CORRECTION

PATENT NO. : 7,285,403 B2 Page 1 of 1
APPLICATION NO. : 11/398807
DATED : October 23, 2007
INVENTOR(S) : Thomas W. Jeffries et al.

It is certified that error appears in the above-identified patent and that said Letters Patent is hereby corrected as shown below:

Column 13, claim 1, line 2, "Pichiastipis" should read --Pichia stipitis--.

Signed and Sealed this

Seventeenth Day of June, 2008

JON W. DUDAS
*Director of the United States Patent and Trademark Office*

SEQUENCE LISTING

<160> NUMBER OF SEQ ID NOS: 4

<210> SEQ ID NO 1
<211> LENGTH: 20
<212> TYPE: DNA
<213> ORGANISM: Artificial
<220> FEATURE:
<223> OTHER INFORMATION: Synthetic oligonucleotide

<400> SEQUENCE: 1
tgtgctgcaa ggcgattaag                                            20

<210> SEQ ID NO 2
<211> LENGTH: 21
<212> TYPE: DNA
<213> ORGANISM: Artificial
<220> FEATURE:
<223> OTHER INFORMATION: Synthetic oligonucleotide

<400> SEQUENCE: 2
gaacacacat gaacaaggaa g                                          21

<210> SEQ ID NO 3
<211> LENGTH: 25
<212> TYPE: DNA
<213> ORGANISM: Artificial
<220> FEATURE:
<223> OTHER INFORMATION: Synthetic oligonucleotide

<400> SEQUENCE: 3
ggatcctggt ggaaactatt tctcg                                      25

```
<210> SEQ ID NO 4
<211> LENGTH: 21
<212> TYPE: DNA
<213> ORGANISM: Artificial
<220> FEATURE:
<223> OTHER INFORMATION: Synthetic oligonucleotide

<400> SEQUENCE: 4
ccaacaaagt gaacagaatc c                                              21
```